US009255920B1

(12) United States Patent
Lamberti et al.

(10) Patent No.: US 9,255,920 B1
(45) Date of Patent: *Feb. 9, 2016

(54) WIRELESS SENSOR

(71) Applicants: Consolidated Nuclear Security, LLC, Reston, VA (US); University of Tennessee Research Foundation, Knoxville, TN (US)

(72) Inventors: Vincent E. Lamberti, Oak Ridge, TN (US); Layton N. Howell, Jr., Knoxville, TN (US); David K. Mee, Knoxville, TN (US); Michael J. Sepaniak, Knoxville, TN (US)

(73) Assignees: Consolidated Nuclear Security, LLC, Reston, VA (US); University of Tennessee Research Foundation, Knoxville, TN (US)

( * ) Notice: Subject to any disclaimer, the term of this patent is extended or adjusted under 35 U.S.C. 154(b) by 49 days.

This patent is subject to a terminal disclaimer.

(21) Appl. No.: 14/493,811

(22) Filed: Sep. 23, 2014

Related U.S. Application Data

(63) Continuation-in-part of application No. 13/832,873, filed on Mar. 15, 2013, now Pat. No. 8,871,523.

(51) Int. Cl.
| | |
|---|---|
| *G01N 33/22* | (2006.01) |
| *G01N 27/74* | (2006.01) |
| *G01N 27/72* | (2006.01) |
| *G01N 1/22* | (2006.01) |
| *G01N 33/00* | (2006.01) |

(52) U.S. Cl.
CPC ............ *G01N 33/0057* (2013.01); *G01N 27/72* (2013.01)

(58) Field of Classification Search
CPC ....... G01N 1/22; G01N 1/2273; G01N 27/72; G01N 27/74; G01N 27/80; G01N 33/0004; G01N 33/0057; G01N 33/20; G01N 33/203; G01N 33/22; G01N 33/227
USPC ............... 436/73, 84, 149, 150, 151, 181; 422/68.1, 69, 83, 88
See application file for complete search history.

(56) References Cited

U.S. PATENT DOCUMENTS

| | | | | |
|---|---|---|---|---|
| 5,821,129 | A * | 10/1998 | Grimes et al. | ................. 436/151 |
| 6,270,591 | B2 | 8/2001 | Chiriac et al. | |
| 6,393,921 | B1 | 5/2002 | Grimes et al. | |
| 7,694,346 | B2 * | 4/2010 | Adams et al. | ..................... 850/7 |
| 7,824,619 | B1 * | 11/2010 | Aviram | .......................... 422/88 |
| 8,871,523 | B1 * | 10/2014 | Lamberti et al. | .............. 436/149 |

(Continued)

OTHER PUBLICATIONS

Ong et al. Sensors, vol. 3, 2003, pp. 11-18.*

(Continued)

*Primary Examiner* — Maureen Wallenhorst
(74) *Attorney, Agent, or Firm* — Michael J. Renner, Esq.; Luedeka Neely Group, P.C.

(57) ABSTRACT

Disclosed is a sensor for detecting a target material. The sensor includes a ferromagnetic metal and a molecular recognition reagent coupled to the ferromagnetic metal. The molecular recognition reagent is operable to expand upon exposure to vapor or liquid from the target material such that the molecular recognition reagent changes a tensile stress upon the ferromagnetic metal. The target material is detected based on changes in the magnetic switching characteristics of the ferromagnetic metal caused by the changes in the tensile stress.

14 Claims, 4 Drawing Sheets

(56) References Cited

U.S. PATENT DOCUMENTS

2006/0032289 A1* 2/2006 Pinnaduwage et al. ...... 73/25.05
2006/0231420 A1* 10/2006 Garzon et al. ................ 205/775

OTHER PUBLICATIONS

Ong et al. IEEE Sensors Journal, vol. 6, No. 3, Jun. 2006, pp. 514-523.*

M.D. Allendorf, et al.; "Stress-Induced Chemical Detection Using Flexible Metal-Organic Frameworks"; J. Am. Chem. Soc. 130 (2008) 14404.

Chiriac, et al; "Effect of Glass Removal on the Magnetic Behavior of FeSiB Glass-Covered Wire"; IEEE Trans. Magn. 33 (1997) 782.

H. Chiriac, et al.; "Amorphous Glass-Covered Magnetic Wires: Preparation, Properties, Applications"; Progress in Materials Science, 1996, 40, 333-407.

C.A. Grimes, et al.; Wireless Magnetoelastic Resonance Sensors: A Critical Review, Sensors 2, (2002) 294.

C.A. Grimes, et al.; "Magnetoelastic Sensors in Combination with Nanometer-scale Honeycombed Thin Film Ceramic $TiO_2$ for Remote Query Measurement of Humidity"; Journal of Applied Physics, 87 (2000).

C.A. Grimes,e t al.; "Remote Query Pressure Measurement Using Magnetoelastic Sensors"; Rev. Sci. Instrum. 70 (1999) 4711.

M. Han, et al.; "Sensors Development Using Its Unusual Properties of Fe/Co-Based IAmorphous Soft Magnetic Wire"; J. Mater. Sci. 40 (2005) 5573.

J. Kravcak, et al.; "The Analysis of Large Barkhausen Effect in the FeSiB Amorphous Wire"; Cxech. J. Phys. 52 (2002) 175.

H. Lai, et al.; Identification of Volatile Chemical Signatures from Plastic Explosives by SPME-GC/MS and Detection by Ion Mobility Spectometry, Anal. Bioanal. Chem. 396 (2010) 2997.

K. Mohri, et al.; "Advances of Amorphous Wire Magnetic over 27 Years"; Phys. Status Solidi A, 206, pp. 601-607, Feb. 2, 2009.

D.S. Moore; "Recent Advances in Trace Explosives Detection Instrumentation"; Sens. Imaging 8 (2007) 9.

D.S. Moore; "Instrumentation for Trace Detection of High Explosives"; Rev. Sci. Instrum. 75 (2004) 2499.

M. Nambayah, et al.; "A Quantitative Assessment of Chemical Techniques for Detecting Traces of Explosives at Counter-Terrorist Portals"; Talanta 63 (2004) 461.

K.G. Ong, et al.; "Quantification of Multiple Bioagents With Wireless, Remote-Query Magnetoelastic Microsensors"; IEEE SEnsors Journal, vol. 6, No. 3, Jun. 2006.

K.G. Ong, et al.; "A Wireless, Passive, Magnetically-soft Harmonic Sensor for Monitoring Sodium Hypochlorite Concentrations in Water"; Sensors 2003, pp. 11-18.

J. M. Perr, et al "Solid Phase Microextraction Ion Mobility Spectrometer Interface for Explosive and Taggant Detection"; J. Sep. Sci. 28 (2005) 177.

L.P. Shen, et al.; "Sensitive Stress-Impadence Micro Sensor Using Amorphous Magnetostrictive Wire"; IEEE Trans. Magn. 33 (1977) 3355.

J.I. Steinfeld, et al.; "Explosives Detection: A Challenge for Physical Chemistry", Annu. Rev. Phys. Chem. 49 (1998) 203.

M. Vazquez; "Soft Magnetic Wires"; Physica B 299 (2001)302.

M. Vazquez, et al.; "Magnetic Properties of Glass-Coated Amorphous and Nanocrystalline Microwires"; J. Magn. Magn. Mater. 160 (1996) 223.

A. Zhukov, et al.; "Microwires Coated by Glass: A New Family of Soft and Hard Magnetic Materials"; J. Mater. Res. 15 (2000) 2107.

* cited by examiner

WIRELESS SENSOR

CROSS-REFERENCE TO RELATED APPLICATION

This application is a continuation-in-part to U.S. application Ser. No. 13/832,873 filed Mar. 15, 2013, now U.S. Pat. No. 8,871,523, issued on Oct. 28, 2014, and entitled "Wireless Sensor for Detecting Explosive Material," the entire contents of which are incorporated by reference herein.

GOVERNMENT RIGHTS

The U.S. Government has rights to this invention pursuant to contract number DE-NA0001942 between the U.S. Department of Energy and Consolidated Nuclear Security, LLC.

FIELD AND BACKGROUND

This disclosure relates to the field of sensors for detecting various target materials. More particularly, this disclosure relates to an inexpensive, highly sensitive sensor having a sensing element capable of being embedded in unobtrusive objects and/or interrogated wirelessly that can be configured to detect a wide range of target materials. Such a sensor is lacking in the prior art.

SUMMARY

According to one embodiment of the disclosure, a sensor for detecting a target material is disclosed including a housing, a ferromagnetic metal disposed in the housing, and a molecular recognition reagent coupled to the ferromagnetic metal. The molecular recognition reagent is operable to expand upon exposure of the target material such that the molecular recognition reagent changes a tensile stress upon the ferromagnetic metal.

According to certain embodiments, the ferromagnetic metal is an amorphous wire preferably composed of a cobalt and iron based alloy. In an alternate embodiment, the ferromagnetic metal is an iron based alloy.

According to certain embodiments, the sensor further includes a detection mechanism having an inducing mechanism to induce alternating magnetic domains in the ferromagnetic metal and a detection mechanism to detect changes in magnetic switching characteristics of the ferromagnetic metal caused by the inducing mechanism and changes in the tensile stress of the ferromagnetic metal caused by exposure of the target material by the molecular recognition reagent.

According to another embodiment of the disclosure, a sensor for detecting the presence of one or more target materials in a target device includes a housing, a first sensing element disposed in the housing, and a second sensing element disposed in the housing. The first sensing element includes a first ferromagnetic metal and a first molecular recognition reagent coupled to the first ferromagnetic metal. The first molecular recognition reagent is operable to expand upon exposure of the one or more target materials such that the first molecular recognition reagent changes a first tensile stress upon the first ferromagnetic metal. The second sensing element includes a second ferromagnetic metal and a second molecular recognition reagent coupled to the second ferromagnetic metal. The second molecular recognition reagent is operable to expand upon exposure of the one or more target materials such that the second molecular recognition reagent changes a second tensile stress upon the second ferromagnetic metal. The second molecular recognition reagent is composed of a different composition than the first molecular recognition reagent such that the second sensing element responds differently than the first sensing element to the one or more target materials.

According to yet another embodiment of the disclosure, a method of detecting one or more target materials in a target device includes the steps of providing a sensor element including a ferromagnetic metal and a molecular recognition reagent coupled to the ferromagnetic metal; placing the sensor element in proximity to or inside the target device such that the molecular recognition reagent expands upon exposure of the one or more target materials and the molecular recognition reagent changes a tensile stress upon the ferromagnetic metal; and detecting a change in the magnetic switching characteristics of the ferromagnetic metal resulting from the tensile stress imparted by the expansion of the molecular recognition reagent.

BRIEF DESCRIPTION OF THE DRAWINGS

Various advantages are apparent by reference to the detailed description in conjunction with the figures, wherein elements are not to scale so as to more clearly show the details, wherein like reference numbers indicate like elements throughout the several views, and wherein.

DETAILED DESCRIPTION

In the following detailed description of the preferred and other embodiments, reference is made to the accompanying drawings, which form a part hereof, and within which are shown by way of illustration the practice of specific embodiments of the disclosure. It is to be understood that other embodiments may be utilized, and that structural changes may be made and processes may vary in other embodiments. Further, it should be understood that this technology may be used in small, low-cost chemical sensors that have applications in many fields such as detecting materials used in making explosives, chemical and biological warfare agents, volatile organic compounds, poisons and toxins, diagnostic exhaled gases, temperature, waste stream contents, air and water pollutants and pathogens, food-borne pathogens, exhaled gases for diagnostics, pharmaceuticals and drugs (including narcotics), cadaverine, diaper contents, moisture, glucose (e.g., blood clot prediction), hazardous gases (e.g., carbon monoxide/natural gas for home detection, methane for coal mine safety, etc.), and countless other chemical substances for countless applications. A particular substance being detected is referred to herein as a "target material." The device or housing that potentially contains one or more target materials is referred to herein as a "target device."

Figure 1:
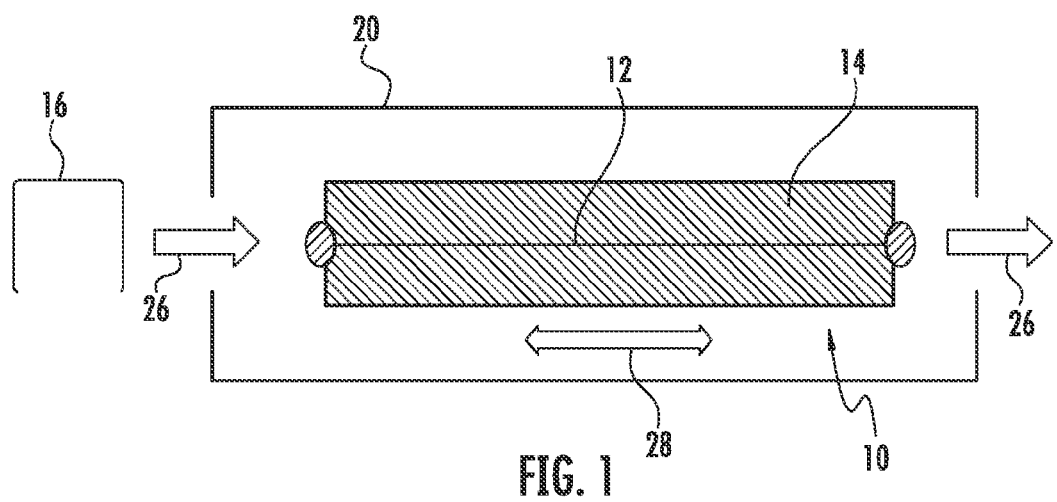
FIGS. 1 and 2 depict different embodiments of a sensing element having a magnetic wire coupled with a molecular recognition reagent according to the disclosure.

Referring to FIG. 1, the sensor of the present disclosure includes a sensing element 10 that employs a ferromagnetic metal 12 coupled to a porous or perforated molecular recognition reagent 14. As shown in FIG. 1, the ferromagnetic metal in certain embodiments is configured as a mounted wire 12 and the molecular recognition reagent 14 is disposed around the wire. Alternatively, the molecular recognition reagent 14 could be coated onto the wire. A ribbon construction for the ferromagnetic metal may also be utilized within the spirit of the present disclosure. For purposes of illustration, the thickness of the molecular recognition reagent 14 in FIG. 1 has been greatly exaggerated with respect to the magnetic wire 12. In typical embodiments, the wire 12 will be about 25 to 40 microns in diameter and the molecular recognition reagent 14 will be about a micron or less in thickness. It should be understood that the term molecular recognition reagent 14 could refer to a specific material or a composite of more than one material.

In operation, the sensing element 10 is placed in proximity to a target device 16 such that the molecular recognition reagent 14 is exposed to vapor or liquid from the target material if the target material is present in the device 16. As shown in the embodiment of FIG. 1, the sensing element 10 may be disposed in a flow housing 20 having a first opening 22 and a second opening 24 such that the target material of the target device 16 flows through the housing 20 and past the sensing element 10 as indicated by arrows 26. The molecular recognition reagent 14 is characterized by its affinity for gaseous or liquid components of particular target materials, and its ability to exhibit a large volume change per unit of the target material absorbed. Thus, when detecting the target device 16, the molecular recognition reagent 14 expands upon exposure to the target material, which imposes stress on the magnetic wire 12 in both directions indicated by arrow 28. The sensing element 10 exploits the fact that, when subjected to alternating magnetic fields, the magnetic field strength and switching speed of the magnetic wire 12 varies as a function of tensile stress in the ferromagnetic wire 12 caused by the volume change of the molecular recognition reagent 14.

In certain embodiments, the sensing element 10 will employ an array of ferromagnetic wires 12 coupled to a diverse set of molecular recognition reagents 14 such that each wire 12 will respond differently to each type or combination of target materials absorbed by the molecular recognition reagents 14. A neural network or other type of artificial intelligence based tool may then be employed to analyze and interpret the changes in the magnetic properties of the wires 12 to identify the presence of the target materials. In other words, while every wire 12 and molecular recognition reagent 14 combinations in the array might react with every target material, the sensor employs computer learning algorithms that will detect different responses of all the wire/reagent combinations and will continually improve as new data regarding the detection of various materials becomes available. As each wire 12 responds differently to each target material, an effective "fingerprint" for each material is generated and the artificial intelligence tool is utilized to interpret the fingerprint and identify the target materials in the target device.

In preferred embodiments, the magnetic wire 12 is an amorphous wire constructed from a ferromagnetic alloy having one or more glass forming components. The amorphous wire is preferably a Cobalt (Co) and Iron (Fe) based alloy such as $Co_{80.9}Fe_{4.4}Nb_{4.5}Si_{8.7}B_{1.5}$ with a diameter of about 25 to 40 microns. In an alternate embodiment, the wire 12 is an iron-based alloy (i.e., predominantly composed of iron). However, the particular combination of components and dimensions of the wire can be tailored for specific applications and an array of sensing elements 10 may include wires of varying alloys and/or diameters including diameters from about 5 to 125 microns. The amorphous characteristic of the wire 12 is produced during the alloy casting operation by rapid cooling from the molten to solid state. As a result, the material has a disordered atomic-scale (noncrystalline) structure. This noncrystalline structure leads to a higher tensile strength than that of material with an orderly structure. Further, the amorphous wire 12 has high magnetic susceptibility with low coercivity and high electrical resistance. Thus, the magnetic domains of the wires 12 can be switched when subjected to very small alternating magnetic fields. In addition, the amorphous wire magnetic domain switching properties are sensitive to stress. These properties of the amorphous magnetic wire 12 enable the sensing applications of the disclosed explosive sensors as further described below.

The molecular recognition reagents 14 are chosen from reactive materials that are operable to expand upon exposure and/or absorption of vapor and/or liquid from the target materials. The space from which the molecular recognition reagents are chosen is large, and the choice generally depends on the particular target substance (e.g., explosive, chemical or biological warfare agent, pharmaceutical, moisture, etc.) that the sensor is intended to detect and the environment conditions in which the device is to be used. Such molecular recognition reagents include, but are not limited to high molecular-weight polymers, solid-phase microextraction (SPME) materials, metal-organic frameworks (MOFs), immobilized antibodies, classical zeolites, and other porous polymers and metals and combinations thereof. Specific examples of molecular recognition reagents include, without limitation, the following: polyacrylic acid (PAA), polyhydroxyethyl methacrylate, dimethacrylate (EDMA), methacrylic acid (MAA), methyl cellulose, polyethyleneimine (PEI), polyethylene oxide (PEO), polypropylene (PP), polystyrene (PS), polydimethylsiloxane (PDMS), Calix[6]arene (Cal[6]), Heptakis(6-O-tert-butyldimethylsilyl-2,3-di-O-acetyl)-β-cyclodextrin (cyclodextrin or CD), electrospun polymers, Kraton® polymers (a synthetic replacement for rubber), and composites thereof. As mentioned above, the sensing element 10 will preferably employ a diverse set of molecular recognition reagents 14 such that each wire 12 will respond differently to each type of target material absorbed by the molecular recognition reagents 14. Further, the particular configuration of the molecular recognition reagents 14 may vary based on the particular target material to be detected. In this regard, the choice of particular molecular recognition reagents 14 is generally based on considerations such as pore size, pore shape, polarity, etc. as compared to the target materials being detected. For example, in embodiments where the sensor is intended to detect large molecules such as provided in anthrax, the molecular recognition reagent may include an imprintable polymer having a "lock and key" arrangement for targeting the particular shape of anthrax molecules. In other words, in the "lock and key" arrangement, the reagent surface includes specific geometric shapes complementary to the shapes of targeted particles.

It is further noted that molecular recognition reagents 14 may also be fabricated from biological materials such as enzymes, antibodies, and aptamers (small single-stranded DNA or RNA molecules) to have lock-and-key relationships with specific substrates. Also, regarding molecular recognition reagents 14 made from composite materials, some of the materials as identified above are used at least in part to improve the able to fabricate the molecular recognition reagents 14. This is particularly true of a cyclodextrin/poly (ethylene oxide) (CD/PEO) mixture. In this regard, CD by itself is difficult to be machined into a molecular recognition reagent 14 of a proper shape and size from a pressed disk due to its friability, but addition of a certain amount of PEO makes the material much more workable. Considering that the composite reagents are physical mixtures—that is, they are typically mixed and pressed rather than reacted—countless combinations of molecular recognition. reagents 14 are possible, such as the CD/PEO mixture, to detect each target material.

Figure 2:
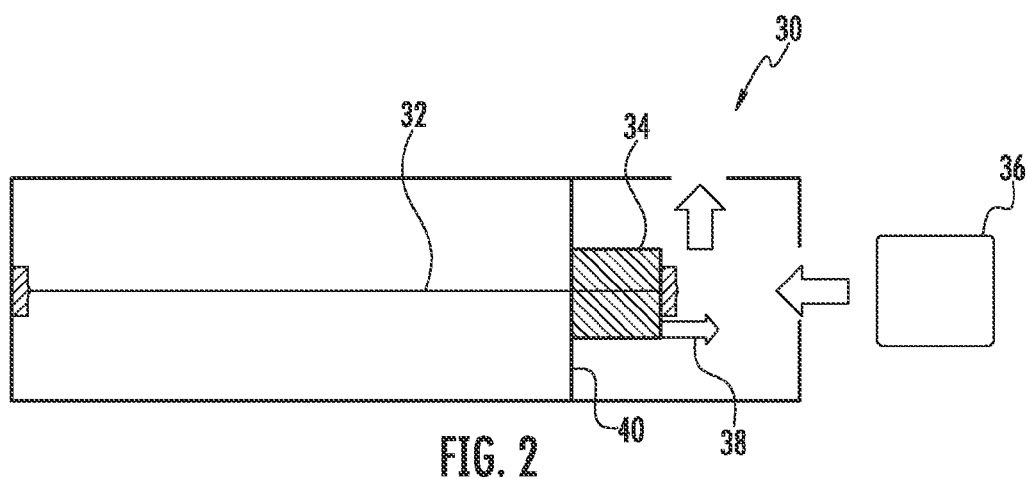

Referring to FIG. 2, an alternate embodiment of a sensing element 30 is shown in which the molecular recognition reagent 34 is secured to both the ferromagnetic wire 32 and a fixed support 40. When detecting a target device, the molecular recognition reagent 34 expands away from the fixed support 40 which imposes stress on the magnetic wire 32 in one direction as indicated by arrow 38. In yet another potential embodiment, the ferromagnetic wire is placed under tension through the use of a tension inducing mechanism such as a spring such that, when the molecular recognition reagent 34 expands upon absorption of a target material, the molecular recognition reagent relieves the tension generated by the tension inducing mechanism.

In operation, a sensing element substantially as described above is placed in proximity to a target device such that the molecular recognition reagent of the sensing element expands upon absorption of vapor or liquid from a target material while an inducing mechanism is used to induce alternating magnetic domains in the ferromagnetic wire of the sensor. The expansion of the molecular recognition reagent changes a tensile stress upon the ferromagnetic wire, and a detection mechanism is used to detect changes in the switching properties of the ferromagnetic wire as a function of changes in the tensile stress of the wire.

Figure 3:
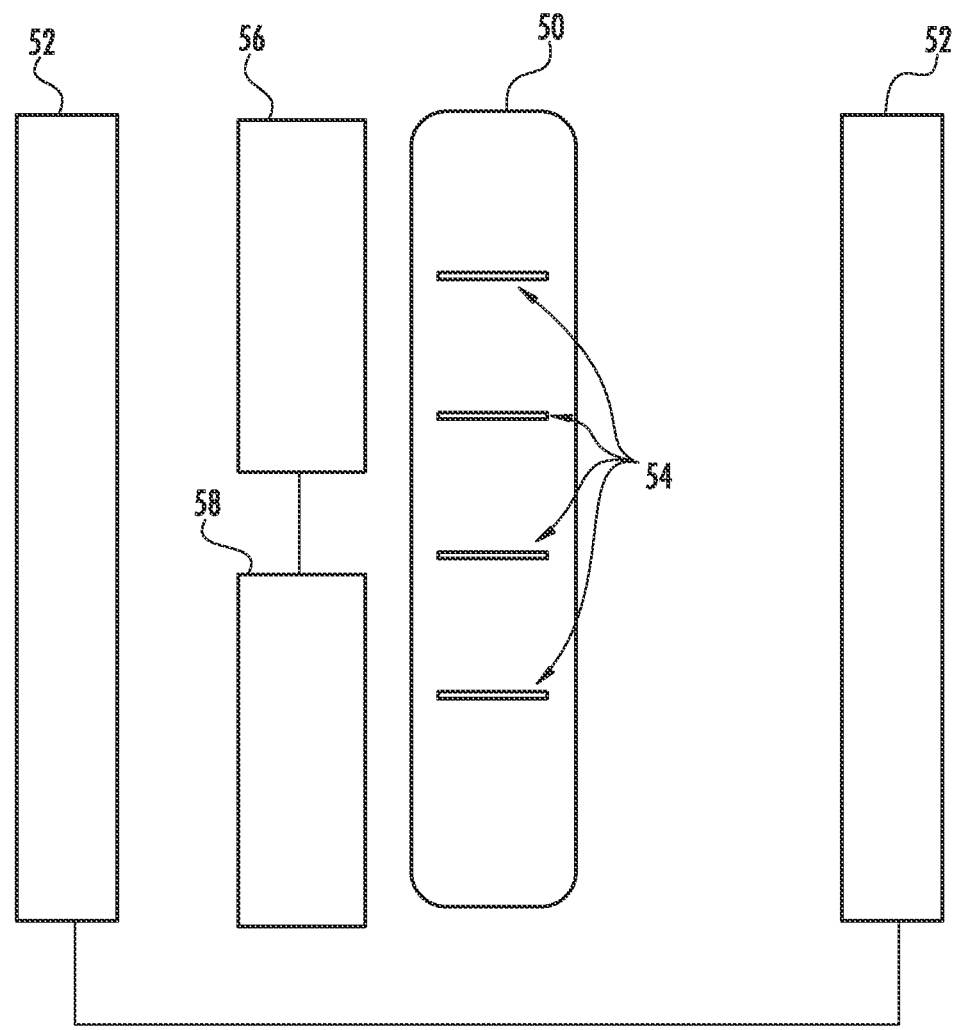
FIG. 3 depicts a schematic illustration of a sensing element detection mechanism according to the present disclosure.

FIG. 3 schematically illustrates a sensor 50 according to the present disclosure where one or more sensing elements 54 are detected by a detection mechanism composed of a system of at least one drive coil 52 and at least one pickup coil 56. Sensor 50 includes the sensing elements 54 positioned such that changes in the magnetic switching characteristics of the sensing elements 54 caused by drive coil 52 is detected by one or more pickup coils 56. An alternating current in the drive coil 52 creates the magnetic field, which continually reverses the magnetic domains in the amorphous wire of the sensing elements 54. Reversal of the magnetic domains is detected with the pickup coil 52 as a peak, which changes height based on tensile stress applied to the ferromagnetic wires by the molecular recognition reagents. In certain embodiments, one or more cancellation coils 58 may also be provided that are wired in an opposite direction from pickup coil 56. Cancellation coil 58 detects a similar drive coil magnetic field but does not detect a significant amount of the signal produced by switching of the ferromagnetic wire of sensing elements 54. The purpose of the cancellation coil is to cancel most of the magnetic field produced by the drive coils and eddy currents caused by the drive fields in conducting objects near the pickup coils 56.

Sensing element 54, drive coil 52, pickup coil 56, and cancellation coil 58 (if used) may be housed within a single unit sensor having a power source and wired or wireless communication means for transmitting data acquired from the sensing element 54, or the drive coil 52, pickup coil 56, and cancellation coil 58 (if used) may be provided in a separate unit from the sensing element 54.

Benefits of a sensor such as those described above include the fact that the sensing element does not require radioactive sources and, in embodiments where the drive 52 and pickup coils 56 are provided in a separate unit from the sensing element 54, the sensing element does not require any type of physical power source or data transfer connection. Further one pickup coil is capable of detecting multiple sensing elements having various molecular recognition reagents without tedious alignment of the sensing elements. Thus, the sensor is small, inexpensive, and portable while offering the benefits of rapid detection while being highly selective and sensitive.

Figure 4A:
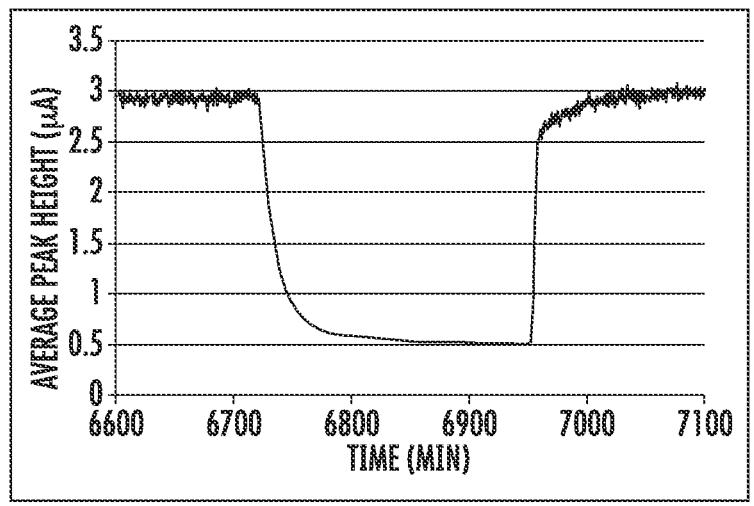
FIGS. 4A-4C depict peak height detection graphs for detecting methanol using a variety of molecular recognition reagents according to the disclosure.
Figure 4B:
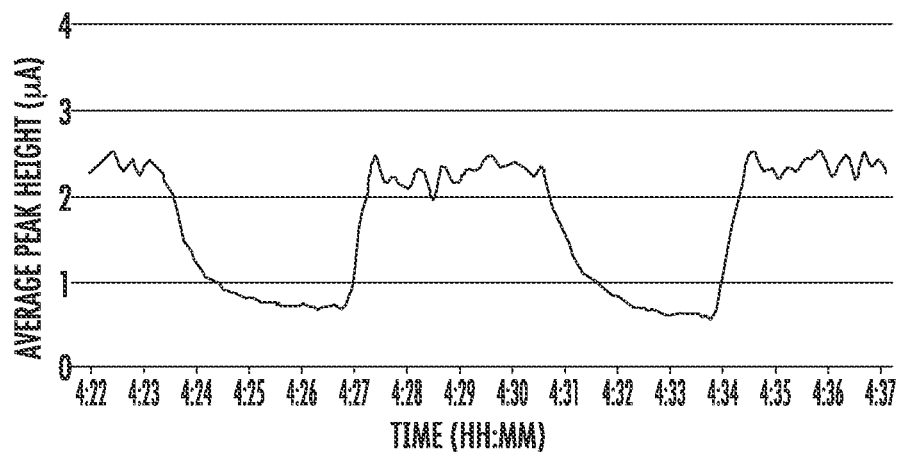
Figure 4C:
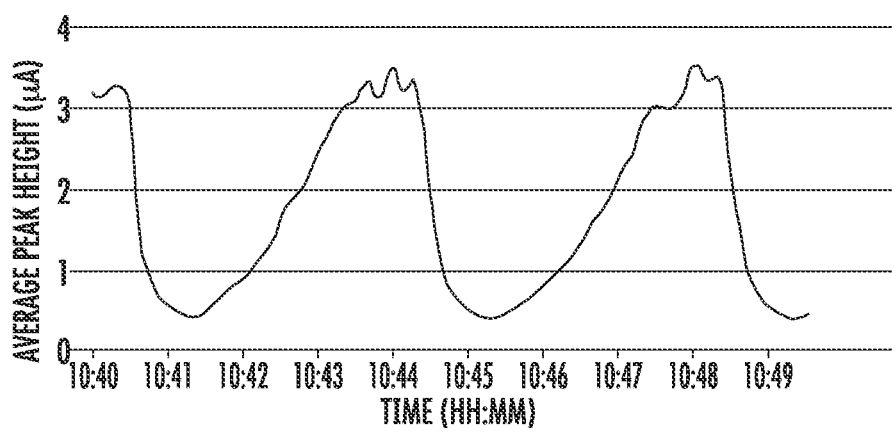

Referring to FIGS. 4A-4C, detection of methanol vapor entrained in a stream of air as an exemplary target material is shown when using a sensing element having various molecular recognition reagents. Referring to FIG. 4A, the molecular recognition reagent is methyl cellulose. Referring to FIG. 4B, the response to methanol of sensing element having a molecular recognition reagent composed of 100% polyethylene oxide (PEO) is provided, whereas FIG. 4C provides the response to methanol where the molecular recognition reagent is composed of 40% α-cyclodextrin and 60% PEO. It is noted that a sensing element having 100% α-cyclodextrin as the molecular recognition reagent is believed not to substantially respond to methanol (i.e., does not create tension in the amorphous wire). The heights of the peaks in the figures are dependent on the speed at which the amorphous wire domains reverse and the strength of the field produced by the wire. As tension is applied to the wire upon absorption of the methanol vapor by the particular molecular recognition reagent, the permeability of the amorphous wire decreases and the domain switching slows. Additionally, the amplitude of the field produced by the wire may decrease. This causes the peak current in the pick-up coil 56 of FIG. 3 to decrease with the increase in tension, which is proportional to the amount and type of explosive material absorbed by the molecular recognition reagent. Slopes and shapes of the falling and rising signals, delay times, and peak heights detected by the pick-up coil may all be useful in determining the identity and concentration of a target and establishing a "fingerprint" for various target materials.

The foregoing descriptions of embodiments have been presented for purposes of illustration and exposition. They are not intended to be exhaustive or to limit the embodiments to the precise forms disclosed. Obvious modifications or variations are possible in light of the above teachings. The embodiments are chosen and described in an effort to provide the best illustrations of principles and practical applications, and to thereby enable one of ordinary skill in the art to utilize the various embodiments as described and with various modifications as are suited to the particular use contemplated. All such modifications and variations are within the scope of the appended claims when interpreted in accordance with the breadth to which they are fairly, legally, and equitably entitled.

What is claimed is:

1. A sensor for detecting a target material comprising:
a housing;
a ferromagnetic metal comprising an amorphous wire disposed in the housing;
a molecular recognition reagent coupled to the ferromagnetic metal, the molecular recognition reagent operable to expand upon exposure to the target material such that the molecular recognition reagent changes a tensile stress upon the ferromagnetic metal;
an inducing mechanism to induce alternating magnetic domains in the ferromagnetic metal; and
a detection mechanism to detect changes in induced peaks along a time waveform resulting from the induced alternating magnetic domains in the ferromagnetic metal and changes in the tensile stress of the ferromagnetic metal caused by exposure of the molecular recognition reagent to the target material.

2. The sensor of claim 1 wherein the amorphous wire is composed of a cobalt and iron based alloy.

3. The sensor of claim 1 wherein the amorphous wire is composed of an iron based alloy.

4. The sensor of claim 1 wherein the detection mechanism and the inducing mechanism are provided in a separate unit from the sensor housing.

5. The sensor of claim 1 wherein no electrical components are provided in the sensor housing.

6. A sensor for detecting the presence of one or more target materials in a target device, the sensor comprising:
a housing;
a first sensing element disposed in the housing including:
a first ferromagnetic metal comprising a first amorphous wire; and
a first molecular recognition reagent coupled to the first ferromagnetic metal, the first molecular recognition reagent operable to expand upon exposure to the one or more target materials such that the first molecular recognition reagent changes a first tensile stress upon the first ferromagnetic metal; and
a second sensing element disposed in the housing including:
a second ferromagnetic metal comprising a second amorphous wire; and
a second molecular recognition reagent coupled to the second ferromagnetic metal, the second molecular recognition reagent operable to expand upon exposure to the one or more target materials such that the second molecular recognition reagent changes a second tensile stress upon the second ferromagnetic metal;
an inducing mechanism to induce alternating magnetic domains in the first and second ferromagnetic metals; and
a detection mechanism to detect changes in induced peaks along a time waveform resulting from the induced alternating magnetic domains in the first and second ferromagnetic metals and changes in the tensile stress of the first and second ferromagnetic metals caused by exposure of the first and second molecular recognition reagents to the one or more target materials,
wherein the second molecular recognition reagent is composed of a different composition than the first molecular recognition reagent such that the second sensing element responds differently than the first sensing element to the one or more target materials.

7. The sensor of claim 6 wherein the first and second amorphous wires are composed of a cobalt and iron based alloy.

8. The sensor of claim 6 wherein the detection mechanism is housed in a separate unit from the sensor housing.

9. The sensor of claim 8 wherein no electrical components are provided in the sensor housing.

10. A method of detecting one or more target materials in a target device comprising:
providing a sensor element including a ferromagnetic metal comprising an amorphous wire and a molecular recognition reagent coupled to the ferromagnetic metal;
placing the sensor element in proximity to or inside the target device such that the molecular recognition reagent expands upon exposure to the one or more target materials causing the molecular recognition reagent to change a tensile stress upon the ferromagnetic metal;
inducing alternating magnetic domains in the ferromagnetic metal; and
detecting a change in magnetic switching characteristics of the ferromagnetic metal resulting from the change in tensile stress imparted by the expansion of the molecular recognition reagent, the change including changes in induced peaks along a time waveform resulting from the induced alternating magnetic domains in the ferromagnetic metal and changes in the tensile stress of the ferromagnetic metal caused by exposure of the molecular recognition reagent to the one or more target materials.

11. The method of claim 10 wherein the amorphous wire is composed of a cobalt and iron based alloy.

12. The method of claim 10 wherein the sensor element includes a plurality of ferromagnetic metal wires each having a different molecular recognition reagent coupled to the wire such that each metal wire responds differently to the one or more target materials of the target device.

13. The method of claim 10 wherein the sensor element includes no electrical components.

14. The method of claim 10 wherein the detecting step is performed by a detection mechanism configured to wirelessly interrogate the sensor element.

* * * * *